US011278290B1

(12) United States Patent
Murphy

(10) Patent No.: US 11,278,290 B1
(45) Date of Patent: Mar. 22, 2022

(54) METHODS FOR TREATMENT OF ADDICTION-REWARD BEHAVIORS

(71) Applicant: Timothy P. Murphy, Providence, RI (US)

(72) Inventor: Timothy P. Murphy, Providence, RI (US)

(*) Notice: Subject to any disclaimer, the term of this patent is extended or adjusted under 35 U.S.C. 154(b) by 1031 days.

(21) Appl. No.: 14/987,876

(22) Filed: Jan. 5, 2016

Related U.S. Application Data

(60) Provisional application No. 62/244,839, filed on Oct. 22, 2015, provisional application No. 62/099,645, filed on Jan. 5, 2015.

(51) Int. Cl.
| | |
|---|---|
| *A61B 17/12* | (2006.01) |
| *A61B 17/122* | (2006.01) |
| *A61B 18/06* | (2006.01) |
| *A61B 18/08* | (2006.01) |
| *A61B 18/12* | (2006.01) |
| *A61B 18/18* | (2006.01) |
| *A61B 17/00* | (2006.01) |
| *A61B 18/00* | (2006.01) |

(52) U.S. Cl.
CPC ...... *A61B 17/12109* (2013.01); *A61B 17/122* (2013.01); *A61B 17/12036* (2013.01); *A61B 18/06* (2013.01); *A61B 18/08* (2013.01); *A61B 18/12* (2013.01); *A61B 18/1815* (2013.01); *A61B 2017/00818* (2013.01); *A61B 2017/00893* (2013.01); *A61B 2018/00404* (2013.01); *A61B 2018/00494* (2013.01); *A61B 2018/00577* (2013.01)

(58) Field of Classification Search
CPC ........... A61B 2018/00404; A61B 2018/00494; A61B 2017/00818; A61B 17/12109; A61B 2017/00778
See application file for complete search history.

(56) References Cited

U.S. PATENT DOCUMENTS 9,572,700 B1 * 2/2017 Kipshidze ............ A61F 5/0076

OTHER PUBLICATIONS

Panagopoulos et al., "The role of ghrelin in addition: a review", published Jun. 20, 2014, Psychopharmacology (2014) 231:2725-2740.*
"Section III: The Action of Heroin (Morphine), 8: Definition of dependence," National Institute on Drug Abuse (NIDA), downloaded Oct. 1, 2018, https://www.drugabuse.gov/publications/teaching-packets/neurobiology-drug-addiction/section-iii-action-heroin-morphine/8-definition-dependence, 2 pp.
Hasin, D. S., et al., "DSM-5 Criteria for Substance Use Disorders: Recommendations and Rationale," Am. J. Psychiatry 2013;170(8):834-851.
Summary Statement, Project Title: Development of Temporary Microspheres for Transcatheter Occlusion of Gastric Arteries: Novel Treatment for Alcohol Use Disorder and Other Addiction-Reward Behaviors, Application No. 1 R43 AA027203-01, Release Date: Apr. 7, 2018, pp. 1-14.

* cited by examiner

*Primary Examiner* — William H Matthews
(74) *Attorney, Agent, or Firm* — Cermak Nakajima & McGowan LLP; Shelly Guest Cermak

(57) ABSTRACT

Methods of treatment of addiction-reward behaviors include reducing ghrelin levels in the patient by at least partially closing at least one artery supplying blood to the stomach, the at least one artery being the celiac artery or a branch of the celiac artery, or by topically treating, surgically removing, or surgically applying treatment to cells in the stomach to reduce ghrelin production by those cells.

6 Claims, 1 Drawing Sheet

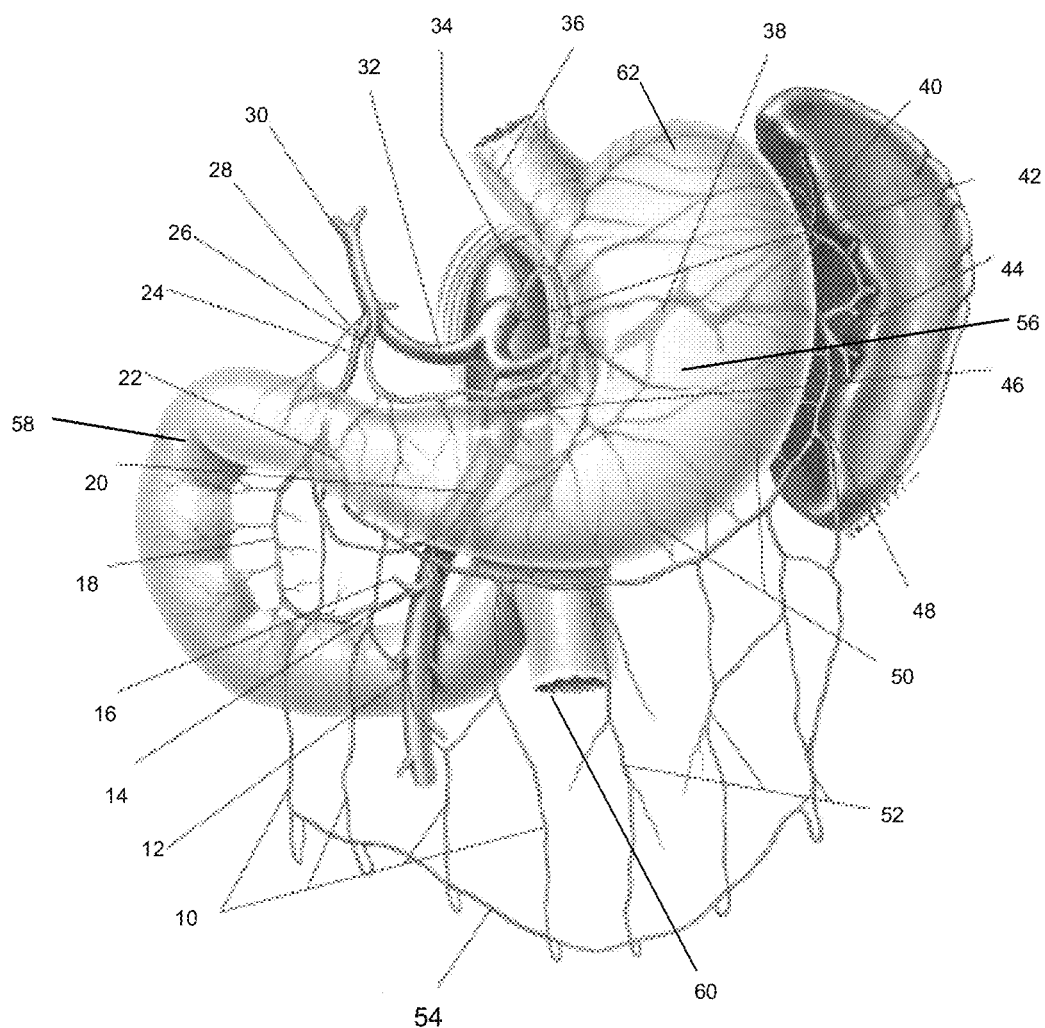

METHODS FOR TREATMENT OF ADDICTION-REWARD BEHAVIORS

This application claims priority under 35 U.S.C. § 119 to U.S. Provisional App. No. 62/099,645, filed 5 Jan. 2015, entitled "Catheter-delivered Transarterial Method for Treatment of Alcohol Dependency", and 62/244,839, filed 22 Oct. 2015, entitled "Catheter-delivered Transarterial Method for Treatment of Addiction-reward Behaviors", the entireties of which are incorporated by reference herein.

BACKGROUND

Field of Endeavor

The present invention relates to devices, systems, and processes useful for the treatment of addiction-award behaviors.

Brief Description of the Related Art

Ghrelin is a 28 amino acid peptide hormone that stimulates appetite, and may be involved in promoting addiction behaviors. For example, ghrelin levels are known to be elevated in individuals with alcohol dependency and cravings for alcohol, and targeting ghrelin receptors using ghrelin antagonists is an increasing area of research in treatment of alcohol dependency (Edwards S, et al., Curr Pharm Des. 2011; 17(14):1323-32; Leggio L, et al. Addict Biol. 2012 March; 17(2):452-64). Ghrelin is produced primarily in cells located in the stomach, mostly concentrated in the gastric fundus. It is known that patients who undergo gastric bypass surgery have lower ghrelin levels afterwards (Cummings D E, et al., N Engl J Med 2002; 346(21):1623-1630; Frühbeck G, et al., N Engl J Med 2004; 350(3):308-309; Tritos N A, et al. Obes Res 2003; 11(8):919-924). Ongoing research into intentional occlusion of arteries that supply this area of the stomach has shown the ability to lower ghrelin levels by 55% (Paxton B E, et al. Radiology. 2013 February; 266(2): 471-9).

Ghrelin receptors are located in the meso-corticolimbic system of the brain, including areas known to be important in addiction-reward behaviors such as the ventral tegmental area (VTA)(Abizaid A, et al. J Neuroendocrinol 2009; 21:787-93). Ghrelin administration into the brains of rats increase dopaminergic activity, which is associated with pleasure or reward feelings and is similar to what occurs after drug abuse (Abizaid A, et al. J Clin Invest 2006; 116:3229-3239). Circulating ghrelin levels have been shown to be elevated in the early-abstinence period in people with alcohol-use disorder (AUD) (Koopman A, et al. Psychoneuroendocrinology 2012; 37, 980-986), and when injected into cerebral ventricles in rats has been shown to increase their alcohol consumption (Jerlhag E, et al. Proc. Natl. Acad. Sci. U.S.A. 2009; 106, 11318-11323). Ghrelin administration increases cocaine-induced conditional place preference and hyperlocomotion (Davis K W, et al. Regul Pept 2007; 140:148-52; Wellman P J, et al. Regul Pept 2008; 146:33-37), increases heroin self-administration in animals (Maric T, et al. Addict Biol 2012; 17:613-622), and increases endocannabinoids in brains of experimental animals (Kola B, et al. PLoS One. 2008 Mar. 12; 3(3):e1797). It is believed that the orexigenic effect of ghrelin is mediated through endogenous cannabinoids in the brain (Kola B, et al. PLoS One. 2008 Mar. 12; 3(3):e1797). Ghrelin levels correlate positively with self-administration of stimulants in animal models (Tessari M, et al. Addict Biol 2007; 12:22-29), and blocking ghrelin receptors in the brain reduces nicotine- and stimulant-induced locomotor sensitization (Wellman P J, et al. Regul Pept 2011; 172:77-80). Administration of ghrelin in humans has been shown to correlate with increased alcohol craving (Leggio L, et al. Psychoneuroendocrinology. 2013 December; 38(12):3085-91), active smokers have higher active ghrelin levels than nonsmokers (Langenberg C, et al. J Clin Endocrinol Metab 2005; 90:6448-6453), and genetic studies in humans have implicated polymorphisms of the central ghrelin receptor in addiction to methamphetamines (Suchankova P, et al. PLoS One. 2013 Aug. 20; 8(8):e71284). All of this information indicates a potentially significant role for central ghrelin activity in these various addiction behaviors. Furthermore, other addictive behaviors that don't involve substance abuse, such as addiction to gambling or obsessive-compulsive disorder, have been linked to activation of the same areas of the brain, such as the mesolimbic system and the ventral tegmental area as substance abuse (Reuter J, et al. Nat Neurosci 2005; 8: 147-148. Sesia T, et al. Int J Neuropsychopharmacol 2013; 16(6):1295-307).

Again using experimental animals, administration of antagonists of the central ghrelin receptor (GHS-R1A) results in less consumption of alcohol (Landgren S, et al. Addict Biol 2011; 17:86-94), reduces effects observed after nicotine administration (Jerlhag E. Drug Alcohol Depend 2011; 117:126-131), and reduces effects of cocaine and amphetamine drug administration (Jerlhag E. Psychopharmacology 2010; 211:415-422). Over-eating, another reward-based behavior mediated in the same areas of the brain, may be treated by reducing blood flow to the stomach (Kipshidze N, et al. JACC Cardiovasc Interv 2015; 8(12):1641-4). These data indicate that reduction in ghrelin or its efficacy could lessen cravings for addictive substances and thereby reduce consumption of those substances.

SUMMARY

According to a first aspect of the invention, in individuals with addiction-reward behaviors, such as alcohol dependency, tobacco dependency, drug addiction, or gambling addiction, embolization of the gastric arteries is used as a method to reduce addiction-reward behaviors. One aspect of the invention includes a method of treating a dependency of a human patient, the dependency being at least in part based on ghrelin levels in the patient, the method comprising reducing ghrelin levels in the patient by at least partially closing at least one artery supplying blood to the stomach, said at least one artery being the celiac artery or a branch of the celiac artery, or topically treating, surgically removing, or surgically applying treatment to cells in the stomach to reduce ghrelin production by said cells.

Another aspect of the invention includes injecting substances into the arteries that supply the stomach, duodenum, or jejunum that hinder the production of ghrelin therein. Another aspect of the invention includes a method of reducing blood flow to the stomach, duodenum, or jejunum to reduce addiction-reward behaviors, such as addiction to drugs or medications, addiction to tobacco, addiction to gambling, or addiction to obsessive-compulsive disorder.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWING

The invention of the present application will now be described in more detail with reference to exemplary embodiments of the apparatus and method, given only by way of example, and with reference to the accompanying drawings, in which the single drawing FIGURE illustrates the arterial circulation of the duodenum, stomach, spleen, liver, pancreas, esophagus, and greater omentum, as well as the anastomotic collaterals.

DETAILED DESCRIPTION OF EXEMPLARY EMBODIMENTS

Referring to the drawing FIGURES, like reference numerals designate identical or corresponding elements throughout the several FIGURES.

The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a range of 1 to 5 should be interpreted to include not only the explicitly recited limits of 1 and 5, but also to include individual values such as 2, 2.7, 3.6, 4.2, and sub-ranges such as 1-2.5, 1.8-3.2, 2.6-4.9, etc. This interpretation should apply regardless of the breadth of the range or the characteristic being described, and also applies to open-ended ranges reciting only one end point, such as "greater than 25," or "less than 10."

As used herein, the term "dependency" means the scientifically-accepted meaning for the particular syndrome to which the term is applied. By way of example, there are 11 symptoms of alcohol use disorder, the presence of any two indicates an alcohol use disorder. Many of these overlap with benzodiazepine addiction. These 11 symptoms are:

1. Alcohol is often taken in larger amounts or over a longer period than was intended;
2. There is a persistent desire or unsuccessful efforts to cut down or control alcohol use;
3. A great deal of time is spent in activities necessary to obtain alcohol, use alcohol, or recover from its effects;
4. Craving, or a strong desire or urge to use alcohol;
5. Recurrent alcohol use resulting in a failure to fulfill major role obligations at work, school, or home;
6. Continued alcohol use despite having persistent or recurrent social or interpersonal problems caused or exacerbated by the effects of alcohol;
7. Important social, occupational, or recreational activities are given up or reduced because of alcohol use;
8. Recurrent alcohol use in situations in which it is physically hazardous;
9. Alcohol use is continued despite knowledge of having a persistent or recurrent physical or psychological problem that is likely to have been caused or exacerbated by alcohol;
10. Tolerance, as defined by either of the following: a) A need for markedly increased amounts of alcohol to achieve intoxication or desired effect b) A markedly diminished effect with continued use of the same amount of alcohol; and
11. Withdrawal, as manifested by either of the following: a) The characteristic withdrawal syndrome for alcohol (refer to criteria A and B of the criteria set for alcohol withdrawal) b) Alcohol (or a closely related substance, such as a benzodiazepine) is taken to relieve or avoid withdrawal symptoms.

Symptoms of narcotic use disorder are (see pcssmat.org/wp-content/uploads/2014/02/5B-DSM-5-Opioid-Use-Disorder-Diagnostic-Criteria.pdf):

1. Opioids are often taken in larger amounts or over a longer period than was intended;
2. There is a persistent desire or unsuccessful efforts to cut down or control opioid use;
3. A great deal of time is spent in activities necessary to obtain the opioid, use the opioid, or recover from its effects;
4. Craving, or a strong desire or urge to use opioids;
5. Recurrent opioid use resulting in a failure to fulfill major role obligations at work, school, or home;
6. Continued opioid use despite having persistent or recurrent social or interpersonal problems caused or exacerbated by the effects of opioids;
7. Important social, occupational, or recreational activities are given up or reduced because of opioid use;
8. Recurrent opioid use in situations in which it is physically hazardous;
9. Continued opioid use despite knowledge of having a persistent or recurrent physical or psychological problem that is likely to have been caused or exacerbated by the substance;
10. Tolerance, as defined by either of the following:
   a. A need for markedly increased amounts of opioids to achieve intoxication or desired effect; and
   b. A markedly diminished effect with continued use of the same amount of an opioid; and
   [Note: This tenth criterion is not considered to be met for those taking opioids solely under appropriate medical supervision.]
11. Withdrawal, as manifested by either of the following:
   a. The characteristic opioid withdrawal syndrome (refer to Criteria A and B of the criteria set for opioid withdrawal); and
   b. Opioids (or a closely related substance) are taken to relieve or avoid withdrawal symptoms.

Symptoms of cocaine or methamphetamine addiction include (www.mayoclinic.org/diseases-conditions/drug-addiction/basics/symptoms/con-20020970):

1. Feeling that you have to use the drug regularly—this can be daily or even several times a day;
2. Having intense urges for the drug;
3. Over time, needing more of the drug to get the same effect;
4. Making certain that you maintain a supply of the drug;
5. Spending money on the drug, even though you can't afford it;
6. Not meeting obligations and work responsibilities, or cutting back on social or recreational activities because of drug use;
7. Doing things to get the drug that you normally wouldn't do, such as stealing;
8. Driving or doing other risky activities when you're under the influence of the drug;
9. Focusing more and more time and energy on getting and using the drug;
10. Failing in your attempts to stop using the drug; and
Experiencing withdrawal symptoms when you attempt to stop taking the drug.

FIG. 1 is a schematic illustration showing the arterial circulation of the duodenum, stomach, spleen, and greater omentum, as well as the anastomotic collaterals, including:

10 Right Ornamental Branches
12 Superior Mesenteric Artery
14 Interior Pancreaticoduodenal Arcade
16 Posterior Pancreaticoduodenal Arcade 18 Anterior Pancreaticoduodenal Arcade
20 Anastomostic Branch to Pancreaticoduodenal Arcade
22 Right Gastroepiploic Artery
24 Gastroduodenal Artery
26 Right Gastric Artery
28 Pyloric Artery
30 Proper Hepatic Artery
32 Common Hepatic Artery
34 Left Gastric Artery
36 Lower Esophageal Arteries
38 Splenic Artery
40 Short Gastric Arteries
42 Celiac Trunk
44 Segmental Splenic Artieries
46 Dorsal Pancreatic Artery
48 Left Gastroepiploic Artery
50 Ascending Gastric Branches
52 Left Ornamental Branches
54 Anastomotic Arcade at the Greater Omemtum
56 Stomach
58 duodenum
60 jejunum
62 gastric fundus In individuals with addiction-reward behaviors, such as alcohol dependency, tobacco dependency, drug addiction, or gambling addiction, embolization of the gastric arteries is used as a method to reduce addiction-reward behaviors. One aspect of the invention is therefore that it includes reducing blood flow to the arteries that supply the stomach, duodenum, or jejunum. Another aspect of the invention includes injecting substances into the arteries that supply the stomach, duodenum, or jejunum that hinder the production of ghrelin therein. Another aspect of the invention includes a method of reducing blood flow to the stomach, duodenum, or jejunum to reduce addiction-reward behaviors, including, but not limited to: addiction to alcohol, drugs or medications; addiction to tobacco; addiction to gambling; and obsessive-compulsive disorder.

Numerous interventional methods, which in the past have been used for other purposes well understood by those of ordinary skill in the art, can be used in the methods described herein. The following includes a discussion of exemplary techniques, which may be used alone or in combination with any other such technique. The methods described herein are not necessarily restricted by the devices that can be used to perform the methods, and numerous commonly commercially available devices, or those described in the existing literature, can be used to perform methods described herein.

Treatment of the lining and/or wall of the stomach, including but not limited to: fulguration or cautery, which are mechanisms of necrosing or destroying cells; radiofrequency ablation; and microwave ablation. All three of these techniques could be performed done using endoscopes introduced via the mouth/esophagus into the stomach, or using laparoscopes, introduced through punctures in the skin and either through the stomach wall into the lumen of the stomach, or by using those forms of energy applied externally to the stomach wall; or by open surgery. Endoscopes, including laparoscopes, which are configured to be able to perform these processes, are well known to those of ordinary skill in the art.

Embolization, or injection of particulate materials into any blood vessels that supply the stomach, to result in reduced flow or occlusion through those vessels. Catheters or other devices capable of such injections, which are configured to be able to perform these processes, are well known to those of ordinary skill in the art.

Injection of drugs, proteins, antibodies, or other materials that interfere with the production of ghrelin, directly into the arteries that supply the stomach, using a catheter(s) introduced into the arteries either by percutaneous (transluminal) or surgical methods. Catheters or other devices capable of such injections, which are configured to be able to perform these processes, are well known to those of ordinary skill in the art.

Chemical ablation by either direct injection of caustic chemicals into the wall of the stomach either from its internal lumen using an endoscope introduced via the mouth/esophagus, or externally injected either percutaneously (through the skin) using imaging guidance or using laparoscopic or open surgical techniques. Endoscopes, including laparoscopes, fluoroscopes cannulae, and the like, which are configured to be able to perform these processes, are well known to those of ordinary skill in the art.

Chemical ablation by injection of caustic chemicals into any of the arteries that supply the stomach (including the left gastric, right gastric, left gastroepiploic, right gastroepiploic, or other branches of the celiac axis) using catheters introduced into the arterial system either percutaneously (transluminal) or using other surgical methods of catheter introduction. Catheters or other devices capable of such injections, which are configured to be able to perform these processes, are well known to those of ordinary skill in the art. See, for example, U.S. Pat. No. 9,208,559.

Flow restriction, using a baffle or flow reducer applied within the lumen of, or externally applied around, the origin or any artery that supplies the stomach. These flow reducers could be applied using catheter introducers, laparoscopically, or using open surgical methods. Catheters or other devices capable of such injections, and the placement of internal flow reduces or baffles, as well as external arterial clamps, clips, and the like which are configured to be able to perform these processes, are well known to those of ordinary skill in the art.

While the invention has been described in detail with reference to exemplary embodiments thereof, it will be apparent to one skilled in the art that various changes can be made, and equivalents employed, without departing from the scope of the invention. The description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

I claim:

1. A method of treating a human patient for alcohol use disorder comprising restricting blood flow to said human patient's stomach, wherein restricting blood flow to said stomach comprises embolization of at least an artery perfusing said stomach.

2. A method of treating a human patient for alcohol use disorder of claim 1, wherein said restricting blood flow is effective to lower serum ghrelin levels.

3. A method of treating a human patient for alcohol use disorder in accordance with claim 1, wherein said embolization comprises transcatheter injection of material into said artery until blood flow in said artery generally ceases.

4. A method of treating a human patient for alcohol use disorder in accordance with claim 1, wherein restricting blood flow to said stomach comprises injecting blocking material through a catheter positioned to deliver said blocking material into a lumen of at least an artery perfusing said stomach until blood flow in said artery generally ceases, said artery selected from the group consisting of a branch of the celiac artery and a gastric artery.

5. A method of treating a human patient for alcohol use disorder in accordance with claim 1, wherein said artery to said stomach is a branch of a celiac artery.

6. A method of treating a human patient for alcohol use disorder in accordance with claim 5, wherein said branch of said celiac artery is a gastric artery.

\* \* \* \* \*